(12) United States Patent
Kaul

(10) Patent No.: US 7,728,139 B2
(45) Date of Patent: Jun. 1, 2010

(54) SOLVENT-FREE PROCESS FOR THE PREPARATION OF DIKETOPYRROLOPYRROLE DERIVATIVES

(75) Inventor: Bansi Lal Kaul, Biel-Benken (CH)

(73) Assignee: MCA Technologies GmbH, Biel-Benken (CH)

( * ) Notice: Subject to any disclaimer, the term of this patent is extended or adjusted under 35 U.S.C. 154(b) by 305 days.

(21) Appl. No.: 10/545,924

(22) PCT Filed: Jun. 24, 2003

(86) PCT No.: PCT/IB03/02710

§ 371 (c)(1),
(2), (4) Date: Aug. 17, 2005

(87) PCT Pub. No.: WO2004/076456

PCT Pub. Date: Sep. 10, 2004

(65) Prior Publication Data

US 2006/0246023 A1    Nov. 2, 2006

(30) Foreign Application Priority Data

Feb. 27, 2003    (WO) .................. PCT/IB03/00758

(51) Int. Cl.
*C07D 487/22* (2006.01)
*C07D 487/02* (2006.01)

(52) U.S. Cl. ..................... 546/49; 548/453

(58) Field of Classification Search ............... 548/453, 548/543, 553; 546/268.1; 549/472, 59
See application file for complete search history.

(56) References Cited

U.S. PATENT DOCUMENTS

| 4,579,949 | A | 4/1986 | Rochat et al. |
|---|---|---|---|
| 4,597,794 | A | 7/1986 | Ohta et al. |
| 4,931,566 | A * | 6/1990 | Surber et al. .............. 548/453 |
| 4,986,851 | A | 1/1991 | Dietz et al. |
| 5,030,669 | A | 7/1991 | Hendrickson et al. |
| 5,085,698 | A | 2/1992 | Ma et al. |
| 5,106,533 | A | 4/1992 | Hendrickson et al. |
| 6,071,989 | A | 6/2000 | Sieber et al. |
| 6,211,347 | B1 | 4/2001 | Sieber et al. |
| 6,302,953 | B1 | 10/2001 | Saikatsu et al. |
| 6,365,720 | B1 | 4/2002 | Schacht et al. |
| 6,462,125 | B1 | 10/2002 | White et al. |

FOREIGN PATENT DOCUMENTS

| EP | 648 817 | 4/1995 |
|---|---|---|
| EP | A 654 711 | 5/1995 |
| EP | 0 962 499 A | 12/1999 |
| WO | WO96/14925 | 5/1996 |
| WO | WO/9832802 | 7/1998 |

OTHER PUBLICATIONS

"Attempted Reformatskii Reaction of Benzonitrile, 1,4-Diketo-3,6-Diphenylpyrrolo[3,4-C]Pyrrole" by Donald G. Farnum et al., *Tetrahedron Letters* No. 29, 1974, pp. 2549-2552.

Heinz Langhals et al., Chromophores Encapsulated in Gold Complexes: DPP Dyes with Novel Properties, Eur. J. Inorg. Chem., 2000, pp. 2345-2349.

Ingo-Peter Lorenz et al., DDP Dyes as Ligands in Transition-Metal Complexes, Chem. Eur. J., 2002, pp. 4047-4055, vol. 8.

English language equivalent abstract to JA2001279238.

* cited by examiner

*Primary Examiner*—Yong Chu
(74) *Attorney, Agent, or Firm*—Norris McLaughlin & Marcus, PA

(57) ABSTRACT

The present application relates to compounds of formula $A(D)_x(E)_y$, (I), compounds of formula (III), compounds of formula (X), as well as processes for the preparation thereof, processes where the compounds (I) are converted to pigments of formula (II) and the use of the compounds (I).

10 Claims, No Drawings

SOLVENT-FREE PROCESS FOR THE PREPARATION OF DIKETOPYRROLOPYRROLE DERIVATIVES

This is an application filed under 35 U.S.C. 371 of PCT/IB2003/002710.

The present invention relates to certain organic compounds, processes for their manufacture, and their use. The invention particularly relates to an essentially solvent-free process for the preparation of the alkali-metal salts of diketopyrrolopyrrole compounds, their use as latent pigments and their use for the preparation of the corresponding diketopyrrolopyrrole pigments in their suitable pigmentary form.

Latent pigments are described in EP-A 654 711, as are chemical, thermal or photolytic methods by means of which it is possible to generate finely divided pigment particles in situ in substrates (see also U.S. Pat. Nos. 6,071,989, 6,211,347 and 6,365,720). It is also known that latent pigments can be used advantageously for the preparation of pigment dispersions, and their use in colouring high molecular mass materials (U.S. Pat. No. 6,211,347).

The process of making pigment derivatives as latent pigments is known from EP 648 817 and WO 98/32802. In those processes, pigments are reacted inter alia with dicarbonates in a solvent, optionally in the presence of a catalyst. A number of solvents are disclosed, including also aromatic solvents such as benzene, toluene, xylene, anisole, chlorobenzene and pyridine. Preference is given to the highly polar solvents N,N-dimethylformamide, N-methyl-pyrrolidone or tetrahydrofuran. In the Examples, only N,N-dimethylformamide, N,N-dimethyl-acetamide or tetrahydrofuran are used.

It has been found, however, that that method does not always yield satisfactory results to the desired extent (see U.S. Pat. No. 6,365,720) some pigments produce inexplicably low yields or can be reacted only partially, with hydroxyl or amide groups. Other pigments react better, but the crude pigment derivatives obtained there from exhibit unsatisfactory purity or inadequate storage stability, so that complex purification steps are necessary. Still further pigments give rise to unexpected problems on a pilot scale or production scale.

In U.S. Pat. No. 6,365,720 it has been claimed that certain pigments can be used with surprisingly better results if the reaction is carried out with a pyrocarbonic acid diester in an aromatic solvent. Both the yield and the purity are markedly higher, and more groups can be incorporated into the pigment. The method according to this invention is also claimed to be excellently suitable especially for the production of latent pigments in relatively large amounts (.gtoreq.1 mol). Furthermore, it is also claimed that surprising a more complete reaction is obtained in, of all things, relatively non-polar solvents in which the pigments and soluble pigment derivatives obtained there from are less soluble than in solvents used hitherto.

Both of these processes suffer from the serious disadvantages of economy and ecology. For example on one hand the processes for the preparation require use of solvents and very difficult to handle reactants, and on the other hand are tedious and too elaborate to be of any commercial importance. More serious disadvantage, however, is the fact that potentially explosive and toxic gases are generated when the pigments are derived from the corresponding latent pigments while being incorporated into the substrate. Thus even the incorporation of latent pigments into the substrates can be extravagant, requiring special equipment and handling measures.

It has now been found that alkali metal salts of certain pigments which are easy to produce and readily hydrolyse or are induced to hydrolyse in situ to generate the corresponding pigment, are better suited as latent pigments particularly for liquid systems such as paints, printing inks and wood stains. They are particularly suitable for the preparation of pigment dispersions, and their use for pigmenting high molecular mass material. The incorporation of such latent pigments does not require any elaborate equipment. Moreover, no potentially hazardous organic volatile materials are liberated thereby. The pigments thus generated in situ are auto-dispersed and do not need further dispersion equipment and/or process.

Accordingly, the invention relates to compounds of formula I

$$A(D)_x(E)_y \tag{I}$$

wherein x and y are each independently of the other an integer from 0 to 6, but x and y are not simultaneously 0, A is the radical or a mixture of radicals of a chromophore of the diketopyrrolopyrrole quinacridone, anthraquinone, perylene, indigo, quinophthalone, indanthrone, isoindolinone, isoindoline, dioxazine, azo, phthalocyanine or perinone series, which radical is bonded via one or more nitrogen atoms to x groups D and via one or more oxygen atoms to y groups E, the nitrogen atoms and oxygen atoms forming part of the radical A, each group D or E independently of any other(s) is an alkali metal.

The invention also relates to a method for preparing a compound of the formula $A(D)_x(E)_y$ (I) by reaction of a compound of the formula II

$$A(H)_x(H)_y \tag{II}$$

with a strong alkali metal base in the presence or absence of an organic solvent at ambient to elevated temperature.

Examples of suitable solvents are primary, secondary or tertiary alcohols containing 1 to 10 carbon atoms, e.g. methanol, ethanol, n-propanol, isopropanol, n-butanol, sec-butanol, tert-butanol, n-pentanol, 2-methyl-2-butanol, 2-methyl-2-pentanol, 3-methyl-3-pentanol, 2-methyl-2-hexanol, 3-ethyl-3-pentanol, 2,4,4-trimethyl-2-pentanol, or glycols such as ethylene glycol or diethylene glycol; and also ethers such as tetrahydrofuran or dioxan, or glycol ethers such as ethylene glycol methyl ether, ethylene glycol ethyl ether, diethylene glycol monomethyl ether or diethylene glycol monoethyl ether; as well as dipolar aprotic solvents such as acetonitrile, benzonitrile, dimethylformamide, N,N-dimethylacetamide, nitrobenzene, N-methylpyrrolidone; aliphatic or aromatic hydrocarbons such as benzene or benzene substituted by alkyl, alkoxy or halogen, e.g. toluene, xylene, anisole or chlorobenzene; or aromatic heterocyclic compounds such as pyridine, picoline or quinoline. A mixture of solvents may also be used. It is convenient to use 5 to 20 parts by weight of solvent per 1 part by weight of reactants.

Suitable strong bases include alkali metal hydroxides, alkali metals such as lithium, sodium and potassium, an alkali metal amide, an alkali metal hydride; and alkali metal or alkaline earth metal alkoxides derived in particular from primary, secondary or tertiary aliphatic alcohols having 1 to 10 carbon atoms. It is also possible to use a mixture of the above mentioned alkali metal alkoxides. Preference is given to using alkali metal alkoxides and hydroxides with alkali metal being especially sodium or potassium, and the alkoxide is preferably derived from a primary, secondary or tertiary alcohol. Particularly preferred strong bases are for example potassium hydroxide, sodium methylate, sodium isopropylate, sodium tert-butylate and sodium tert-amylate. These alkali metal alkoxides can also be prepared in situ by reacting the corresponding alcohol with alkali metal.

If an alcoholate is used as a base, it may also be used as a solution or a suspension in the same alcohol or in an inert solvent. The alcohol and/or the solvent thus used and formed during the reaction may continuously be distilled off during the reaction thereby providing solvent-free reaction conditions.

A is preferably the radical of a chromophore of the diketopyrrolopyrrole, quinacridone, perylene, indigo, quinophthalone, isoindolinone, isoindoline, dioxazine, azo or the perinone series.

Further preference is given to derivatives having at least one immediately adjacent or conjugated carbonyl group at each nitrogen atom bonded to x groups D. It is also possible, however, for a plurality, or even all, of the groups D and/or E to be bonded to such nitrogen or oxygen atoms.

Particularly preferred compounds of formula I are the diketopyrrolopyrrole compounds of formula III

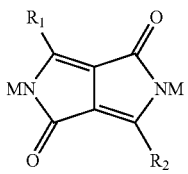

III wherein both M represent an alkali metal and each of $R_1$ and $R_2$ independently of the other is an isocyclic or heterocyclic aromatic radical. The radicals $R_1$ and $R_2$ may be different or identical, but are preferably identical. $R_1$ and $R_2$ as isocyclic aromatic radicals are preferably monocyclic to tetracyclic radicals, most preferably monocyclic or bicyclic radicals, i.e. phenyl, biphenyl or naphthyl. Heterocyclic aromatic radicals $R_1$ and $R_2$ are preferably monocyclic to tricyclic radicals. These radicals may be entirely heterocyclic or may contain a heterocyclic ring and one or more fused benzene rings, and the cyano group can be linked both to the heterocyclic and to the isocyclic moiety respectively. Examples of heterocyclic aromatic radicals are: pyridyl, pyrimidyl, pyrazinyl, triazinyl, furyl, pyrrolyl, thiophenyl, quinolyl, benzimidazolyl, quinazolyl, quinoxalyl, phthalazinyl, phthalazindionyl, phthalamidyl, isoquinolinyl, isothiazolyl, acridinyl, acridonyl, quinazolindionyl, quinoxadindionyl, benzoxazindionyl, benzoxazinonyl and naphthalimidyl.

Both the isocyclic and the heterocyclic aromatic radicals may contain the customary non-watersolubilising substituents such as:

(1) Halogen atoms, e.g. chlorine, bromine or fluorine atoms.

(2) Branched or unbranched alkyl groups containing preferably 1 to 18, especially 1 to 12, more particularly 1 to 8 and, most preferably, 1 to 4 carbon atoms. These alkyl groups may contain non-watersolubilising substituents, e.g. fluorine, —$OCOR_5$, —$OR_6$, —$CONR_7$ or —$CONHR_8$, wherein $R_5$ and $R_6$ are alkyl, aryl such as napthyl, or benzyl or benzyl substituted by halogen, alkyl or alkoxy, or a heterocyclic radical; $R_7$ and $R_8$ are hydrogen, alkyl or alkyl substituted by cyano or hydroxy, or $C_7$-$C_8$ cycloalkyl, aryl or heteroaryl, especially phenyl or phenyl substituted by halogen, alkyl or alkoxy, or $R_7$ and $R_8$ together with the nitrogen atom form a 5- or 6-membered heterocyclic ring, e.g. a morpholine, piperidine or phthalimide ring. Further possible substituents at the alkyl groups are mono- or dialkylated amino groups, aryl radicals such as naphthyl or preferably phenyl or phenyl substituted by halogen, alkyl or alkoxy, or also heterocyclic aromatic radicals such as 2-thienyl, 2-benzoxazolyl, 2-benzthiazolyl, 2-benzimidazolyl, 6-benzimidazolonyl, 2-, 3- or 4-pyridyl, or 2-, 4- or 6-quinolyl radicals.

(3) Alkoxy groups containing preferably 1 to 18, especially 1 to 12, more particularly 1 to 8 and, most preferably, 1 to 4 carbon atoms.

(4) A cyano group.

Examples of unsubstituted or substituted alkyl groups are: methyl, ethyl, n-propyl, isopropyl, n-butyl, sec-butyl, tert-butyl, tert-amyl, n-pentyl, n-hexyl, 1,1,3,3-tetramethylbutyl, n-heptyl, n-octyl, nonyl, decyl, undecyl, dodecyl, hydroxymethyl, trifluoromethyl, trifluoroethyl, cyanomethyl, methoxycarbonylmethyl, acetoxymethyl or benzyl.

Preferred meanings of $R_1$ and $R_2$ are phenyl or phenyl substituted by one or two fluorine, chlorine or bromine atoms or mixtures thereof, by one, two or three methoxy or methyl groups or mixtures thereof with chlorine atoms, by cyano, by dimethylamino, by trifluoromethyl, by alkoxycarbonyl of 2 to 3 carbon atoms, by tert-butyl, by cyanophenyl, by acetyl or by alkylbenzoyloxy of 11-14 carbon atoms; biphenyl; naphthyl or naphthyl substituted by methoxy; anthryl; phenanthryl; pyridyl or pyridyl substituted by methyl or by amyloxy; quinolyl; furyl or thienyl.

Besides the process of making compounds of Formula III from the corresponding preferred compounds of formula IV

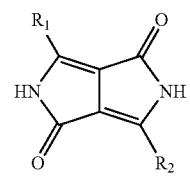

IV of the general formula II, the compounds of Formula III can also be prepared directly by essentially solvent free in situ synthesis, which process comprises reacting 1 mole of a disuccinate of formula

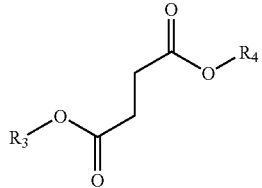

V wherein each $R_3$ and $R_4$ independently of the other is an alkyl or a cycloalkyl or an aryl radical, with at the most 2 moles of a nitrile of the formula $R_1$—CN   (VI)

or $R_2$—CN   (VII)

or with 0.1 to 1.9 mole of a nitrile of the formula VI and 1.9 to 0.1 mole of the nitrile of the formula VII, essentially in the absence of any organic solvent and in the presence of a strong base at elevated temperature. This process for the preparation of pigments of formula IV without use of a solvent is particularly preferred.

It is preferred in this connection to use nitrites of the formulae VI and/or VII, wherein $R_1$ and $R_2$ are unsubstituted phenyl or naphthyl or phenyl or naphthyl, which contain non-watersolubilising substituents.

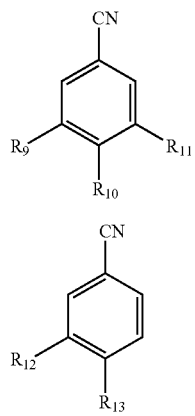

In particular, the starting materials employed are nitrites of the formula VIII wherein each of $R_9$, $R_{10}$ and $R_{11}$ independently of one another is hydrogen, fluorine, chlorine, bromine, cyano, trifluoromethyl, $C_1$-$C_{12}$ alkyl, $C_1$-$C_{12}$ alkoxy, $C_1$-$C_{12}$ alkylmercapto, $C_2$-$C_{13}$ alkoxycarbonyl, $C_2$-$C_{13}$ alkanoylamino, $C_1$-$C_{12}$ monoalkylamino, $C_2$-$C_{24}$ dialkylamino or phenoxy, phenylmercapto, phenoxycarbonyl, phenylcarbamoyl or benzoylamino, each unsubstituted or substituted by halogen, $C_1$-$C_{12}$ alkyl or $C_1$-$C_{12}$ alkoxy, with the proviso that at least one of $R_9$, $R_{10}$ and $R_{11}$ is hydrogen.

Most preferably, the starting materials employed are nitriles of the formula IX wherein one of $R_{12}$ and $R_{13}$ is chlorine, bromine, $C_1$-$C_4$ alkyl, cyano, $C_1$-$C_4$ alkoxy, or phenoxy, carbamoyl or $C_2$-$C_5$ alkylcarbamoyl, each unsubstituted or substituted by chlorine or methyl, or phenylcarbamoyl which is unsubstituted or substituted by chlorine, methyl or methoxy, and the other is hydrogen.

The disuccinates V to be used in the process of this invention may be dialkyl, dicycloalkyl or diaryl. The dialkyl, dicycloalkyl and diaryl succinates may also be unsymmetrical. However, it is preferred to use symmetrical disuccinates, most preferably symmetrical dialkyl succinates.

Examples of disuccinates are dimethyl succinate, diethyl succinate, dipropyl succinate, dibutyl succinate, dipentyl succinate, dihexyl succinate, diheptyl succinate, dioctyl succinate, diisopropyl succinate, di-sec-butyl succinate, di-tert-butyl succinate, di-tert-amyl succinate, di-[1,1-dimethylbutyl]succinate, di-[1,1,3,3-tetramethylbutyl]succinate, di-[1,1-dimethylpentyl]succinate, di-[1-methyl-1-ethylbutyl]succinate, di-[1,1-diethlylpropyl]succinate, diphenyl succinate, di[4-methylphenyl]succinate, di-[2-methylphenyl]succinate, di-[4-chlorophenyl]succinate, monoethyl-monophenyl succinate, and dicyclohexyl succinate.

The disuccinates V and the nitriles of the formula VI or VII are known compounds and may be prepared by known methods.

This particular process of the invention is carried out in the absence of any solvent in the temperature range from 70° C. to 200° C., with the preferred range being from 80° to 140° C.

A process for the synthesis of 1,4-diketo-3,6-diphenylpyrrolo[3,4-c]pyrroles starting from benzonitrile and ethyl bromoacetate in the presence of activated zinc-copper couple is described in Tetrahedron Lett. 1974, 2549-52. However, the yields obtained up to now have been unsatisfactory.

By starting from a succinate and an aromatic nitrile under specific reaction conditions as described in U.S. Pat. No. 4,579,949 the desired pyrrolo[3,4-c]pyrroles are obtained in substantially higher yield. However, the process requires the use of very special inert organic solvents. To obtain high yields as claimed in the patent, besides being inert, the solvents need to be of high purity and particularly substantially anhydrous. Furthermore, the solvents need to be regenerated for reuse after their use in the process. Regeneration of solvents in high purity and particularly in substantially anhydrous form makes the process further cumbersome. Moreover, the use of solvent also reduces the productivity and requires higher energy consumption thereby making the process less economical. For example, the U.S. Pat. No. 4,579,949 also describes the use of 5 to 20 parts by weight of solvent per 1 part by weight of reactants. Other disadvantages of a solvent-based process include environmental (VOC), hygiene and safety issues.

Accordingly, the present invention provides a process for the preparation of 1,4-diketopyrrolo[3,4-c]pyrroles of the formula III essentially in the absence of any organic solvent and in the presence of a strong base at elevated temperature, thereby alleviating the said disadvantages of the state-of-the-art solvent based process. The present invention also provides a process of preparation of the corresponding 1,4-diketopyrrolo[3,4-c]pyrrole pigments of the formula IV in their finely divided suitable pigmentary form.

It is entirely possible to carry out this process not only batch wise, but also continuously. When using disuccinates containing alkyl radicals and alcoholates which are derived from lower alcohols such as methanol, ethanol, n-propanol, isopropanol or tert-butanol, it may be necessary to remove the lower alcohol formed during the reaction from the reaction medium continuously in order to obtain higher yields.

A further preferred embodiment of the process consists in using the nitrile to be reacted with the disuccinate in no more than the stoichiometric proportions. It has been found that the yield of final product can usually be further improved by using an excess of disuccinate over the nitrile, in which case the optimum amount must be determined according to the respective reactants and may be up to 50 percent in excess over the stoichiometric amount required with respect to the nitrile.

Further preferred compounds of the general formula I are the quinacridones of formula X

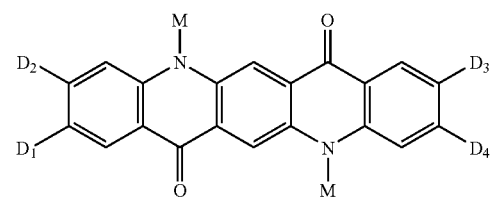

wherein a preferred meaning of M is an alkali metal, $D_1$, $D_2$, $D_3$ and $D_4$ are fluorine, chlorine or bromine atoms or mixtures thereof, methoxy, methyl groups or mixtures thereof, cyano, dimethylamino, trifluoromethyl, tert-butyl or acetyl groups;

the isoindolinone compounds of formula

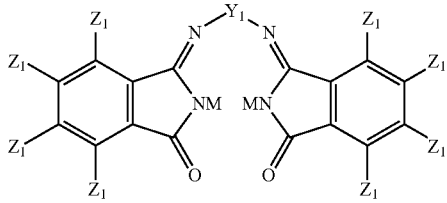

XI wherein M is an alkali metal, preferably sodium or potassium, $Z_1$ halogen or hydrogen, and $Y_1$ is an aromatic residue of the formula

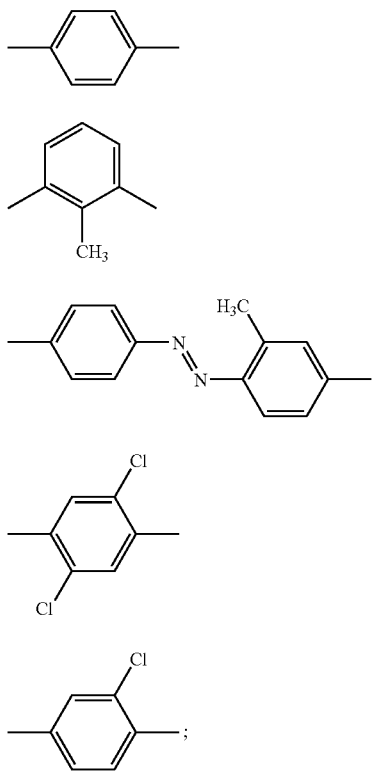

XII

XIII

XIV

XV

XVI the quinophthalone of formula

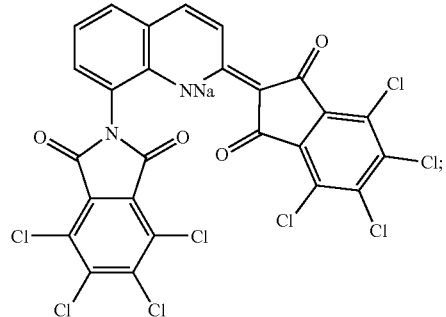

XVII the isoindoline of Formula

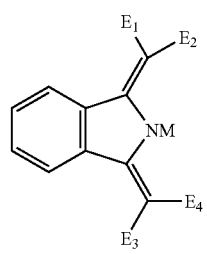

XVIII wherein $E_1$ through $E_4$ represent CN, CONH-alkyl or CONH-aryl. $E_1/E_2$ and $E_3/E_4$ can also be members of a mono- and poly-heterocyclic ring systems or combinations thereof. Examples of such compounds are the derivatives of: C.I. Pigment Yellow 139, C.I. Pigment Yellow 185, C.I. Pigment Orange 66, Pigment Orange 69, Pigment Red 260, Pigment Brown 38.

Further compounds of the formula $A(H)_x(H)_y$ (II) suitable for the formation of the compounds of formula $A(D)_x(E)_y$ (I) are for example
a) the azo pigments: C.I. Pigment Yellow 154, C.I. Pigment Yellow 180, C.I. Pigment Yellow 181, C.I. Pigment Yellow 182, C.I. Pigment Orange 36, C.I. Pigment Orange 62, C.I. Pigment Orange 64, C.I. Pigment Red 176, C.I. Pigment Red 185, C.I. Pigment Brown 23;
b) the perylene pigments: C.I. Pigment Red 224, C.I. Pigment Violet 23;
c) the perinone pigment: C.I. Pigment Orange 43;
d) the anthraquinone pigments: C.I. Pigment Red 177, C.I. Pigment Blue 60;
e) the pyrazoloquinazolone pigments: C.I. Pigment Orange 67, C.I. Pigment Red 251;
f) the phthalocyanine pigment: C.I. Pigment Blue 16;
g) the heterocyclic pigments: thiazine (THI) pigments such as claimed in WO 9832800 and benzimidazolone-dioxazine pigments such as claimed in DE 4442291.

The present invention is also related to a process of making a finely divided particulate compound of formula $A(H)_x(H)_y$ (II) from the corresponding initial crude compound of the same formula.

Production of organic pigments, which are particulate organic solids, usually involves two processing stages (Hugh Smith in Pigment Handbook Vol I page 414, ed. P. Lewis, John Wiley 1988). The first stage involves the synthesis of the corresponding chemical moiety in which the product is usually formed in a large crystalline form not suitable for pigment applications. In a subsequent process the primary particles are sub-divided and then tailored to meet the requirements of their application. Such processes of finishing or conditioning of pigments are, however, usually very energy consuming (such as wet and dry milling) or highly polluting (such as acid pasting or acid swelling). Finishing of organic pigments such as isoindolinone pigments via their alkali metal salts in situ is also described. However, the use of large quantities of an organic solvent is imperative. Moreover, the process also requires the use of very special inert organic solvents. Besides being inert, the solvents need to be substantially anhydrous. Furthermore, the solvents need to be regenerated for reuse in a separate process after their use in the process. Regeneration of solvents, particularly the most preferred alcoholic solvents, in substantially anhydrous form makes the process further cumbersome. Moreover, the use of large quantities of solvent also reduces the productivity and requires higher energy consumption thereby making the process less economical.

The present process has the advantage that the use of solvent is not imperative in the finishing stage. Moreover, if the most preferred alcoholic solvents are used in place of and/or in combination with water, they need not, be anhydrous, thereby making their regeneration very facile and economical. The final pigment composition is obtained with a fine particle size and the desired application properties such as excellent dispersability, high color strength, high weatherability, and high saturation of color.

In a preferred method, water or a mixture of water and a primary or a secondary is used as medium of hydrolysis.

One can also use additives known in the state-of-the-art to control the particle size of the pigment composition. It's possible as well to control the particle size of the pigment composition by heating under pressure the final pigment suspension at the end of the precipitation.

Depending on the pigments and on the conditions of hydrolysis, pigments with a particle size below 2 microns are obtained.

When the formation of the desired particulate crystal size and shape is complete, the conditioned pigment is isolated by filtration, the press cake being washed with water and/or an organic solvent, preferably methanol, followed by water and dried. Good results can be obtained by performing the filtration in acidic conditions.

One can also use additives known in the state-of-the-art to control the particle size of the pigment composition. It's possible as well to control the particle size of the pigment composition by heating under pressure the final pigment suspension at the end of the hydrolysis.

A further objective of the present invention is to provide pigment dispersions, which possess high stability and good transparency, and a process for preparing them.

Recent pigment applications such as color filters and ink jet applications are placing stringent requirements on the coloristic and processing properties of pigments. The pigments are required to possess clean, strong and bright shades to allow the opening-up of a large color area. Furthermore, they should be able to be used not only as an individual pigment but also as an element for combination in, say, trichromatic pigmentations. In terms of technical application it proves advantageous to apply the pigment as dispersion, since it is then possible to avoid laborious mixing and milling operations, which represent an additional hygiene burden. Moreover, the dispersions make the pigmentation process more reproducible, since there is a more homogeneous distribution of the pigment particles than in the powder form.

On economic grounds even for classical applications such as printing inks, it is particularly desirable to employ concentrated, stable dispersions, which require little space on transportation or storage and at the same time possess good stability.

Moreover, for ecological reasons and stringent VOC regulatory considerations in many countries aqueous dispersions rather than solvent-based dispersions are highly desired.

Alkali metal salts of pigments of the present invention used as latent pigments are particularly suitable for preparation of all such pigment dispersions, typically known for example from U.S. Pat. No. 6,302,953; U.S. Pat. No. 6,462,125, 4; U.S. Pat. No. 4,986,851; WO 99/01511; WO 03/008510. Surprisingly, since alkali metal salt pigments get auto-dispersed upon incorporation and by in situ hydrolysis, no special dispersing equipment such as bead-mills or kneaders are required for their dispersion, unlike any state-of-the-art processes for the preparation of pigment dispersions.

Accordingly, from U.S. Pat. Nos. 4,597,794 and 5,085,698 it is known to prepare fine pigment dispersions having an average particle size distribution of 0.015-0.5 micrometers, which are obtained with the addition of stabilising copolymers by mechanical comminution and subsequent selection techniques, such as filtration or centrifuging, in order to remove coarse particles. A disadvantage of these processes is the extremely time-consuming and energy-intensive milling process, which may last for several days and requires high frictional energy. The milled product has a broad particle size distribution and rough surfaces owing to the mechanical stress. Excessively large pigment particles, or those with a roughened surface, lead to a loss of transparency. Smaller particles, on the other hand, tend to form aggregates, which in the course of the dispersion process are broken up by known techniques, by means of high-energy input in the form, for example, of ultrasound. One consequence of the propensity of smaller particles to aggregate is their flocculation tendency, and so these dispersions are inherently unstable.

The disadvantages described can be alleviated only in part by other techniques, such as evaporation methods (see U.S. Pat. Nos. 5,030,669 and 5,106,533) or the preparation of fine dispersions under high pressure (WO 96/14925). Moreover, these techniques require special apparatus for their application.

U.S. Pat. No. 6,211,347 provides a process for preparing pigment dispersions comprising subjecting a mixture comprising a latent pigment known from EP-A 654 711, a polymer and a solvent to thermal, chemical or photolytic treatment. The disadvantages of such latent pigments and particularly the drawbacks of their use as described above are thereby not adequately addressed.

The present invention, accordingly, provides a process for preparing pigment dispersions composed of a pigment, a polymer and/or a dispersant, a liquid medium and optionally an alkali metal salt of an organic acid which comprises 1) incorporating a compound of formula $A(D)_x(E)_y$ (I) into a mixture A of a polymer, a liquid medium, a polymer and/or a dispersant, and then optionally adding an organic acid, or 2) optional incorporation of an organic acid to a mixture B comprising of a compound of formula $A(D)_x(E)_y$ (I), a polymer and/or a dispersant, and a liquid medium, or 3) simultaneous incorporation of a compound of formula $A(D)_x(E)_y$ (I) and an organic acid, into a mixture C comprising a polymer and/or a dispersant and a liquid medium, or any other permutations and combinations of the above procedures.

Organic acids suitable for this process are aliphatic, or aromatic poly-carboxylic or poly-sulphonic acids or polyphosphonic acids containing up to 4 acid groups acids for the each aliphatic or the aromatic rest. Preferred organic acids acid are the ones that, besides interacting with the alkali metal salt of the pigment, can act both as a dispersing as well as an anti-microbial agent. Typical acids are up to C18 aliphatic acids, aromatic acid such as benzoic acids, phthalic acids terephthalic acids, isophthalic acids trimesic acids and pyromelitic acids; benzene, alkylbenzene, naphthalene and alkylnaphthalene sulphonic or phosphonic acids.

Typical state-of-the art liquids are water organic solvents are aliphatic $C_1$-$C_4$ alcohols, such as methanol, ethanol, n-propanol, isopropanol, n-butanol, tert-butanol, ketones such as acetone methyl ethyl ketone, methyl isobutyl ketone or diacetone alcohol, and also polyols, cellosolves and carbitols, such as ethylene glycol, diethylene glycol, triethylene glycol, glycerol, propylene glycol, ethylene glycol monomethyl or monoethyl ether, propylene glycol methyl ether, dipropylene glycol methyl ether, tripropylene glycol methyl ether, ethylene glycol phenyl ether, propylene glycol phenyl ether, diethylene glycol monomethyl or monoethyl ether, diethylene glycol monobutyl ether, triethylene glycol monomethyl or monoethyl ether, and also N-methyl-2-pyrrolidone, 2-pyrrolidone, N,N'-dimethylformamide or N,N'-dimethylacetamide.

However, the process is particularly suitable for the preparation of aqueous pigment dispersions.

The fine pigment dispersions prepared by the process of the invention preferably possess an average particle size distribution of 0.02-0.6 micrometers, with particular preference 0.03-0.5 micrometers and, with very particular preference, 0.06-0.4 micrometers. The particle size distribution was determined by the Joyce-Loebl disk centrifuging method.

The dispersants can be ionic or non-ionic in character, preferably which possess a preferred spatial orientation in solvents of different density. The aqueous dispersions, for example, comprise large molecules consisting of a hydrophilic head and a hydrophobic tail for example Fluorad FC-170, a non-ionic fluorine-containing surfactant from 3M Inc. (or such as OLOA™ 1200 from Chevron Corp., Richfield, Calif., Amoco™ 9250, from Amoco Chemical Co., Naperville, Ill.). The resulting dispersions preferably contain 20% by weight, with particular preference 10% by weight and, with very particular preference, 5% by weight of additives and may if desired include further co-solvents, examples being cyclohexanone, cyclopentanone, N,N'-dimethylformamide and dimethyl sulfoxide.

Polymers for aqueous pigment dispersions are preferably polymers consisting of a hydrophilic and hydrophobic part. The former can be ionisable, and form salts, or non-ionisable.

The polymers are preferably random, block or graft polymers.

The hydrophilic part of the polymers is formed, for example, from monomers which in addition to functional groups such as alcohol, carboxyl, carboxamido, carboxylato or sulfo groups comprise sulfato, cyanato or carboxylic anhydride groups, or ether groups such as ethylene or propylene oxide groups, and in addition a polymerizable vinyl or vinylene radical, such as an acrylic or methylacrylic, crotyl, sulfoethylmethylacrylic, sulfopropylmetlhylacrylic, vinylnaphthyl, vinylphenyl or vinyltolyl radical, itaconyl radical, for example itaconyl monoesters, maleic acid or maleinyl radical, for example maleic monoesters, fumaryl radical, for example fumaryl monoesters, and especially vinylbenzoic acid. The monoesters are for example monoesters of itaconic, maleic or fumaric acid.

Preference is given to monomers which possess carboxyl, carboxylic anhydride, sulfonate or sulfate groups as functional groups. Particular preference is given to carboxyl or carboxylic anhydride groups, for example vinylbenzoic acid or maleic anhydride.

Monomers which form the hydrophobic part of the polymers are preferably for example selected from the group of the apolar monomers consisting of styrene, styrene derivatives, such as $C_1$-$C_4$ alkyl-substituted styrene, and vinyl chloride, vinylnaphthalene, vinylnaphthalene derivatives, such as $C_1$-$C_4$ alkyl-substituted vinylnaphthalene, vinyltoluene, alpha.-, m-, p- or m/p-vinyltoluene and aliphatic $C_{12}$-$C_{18}$ alkenes.

Preferred hydrophobic apolar monomers are for example styrene, vinyltoluene and octadecene.

The copolymers chosen preferably have a narrow molar mass distribution of 1-2 Mw/Mn (where Mw is the mass average and Mn the number average).

For water-free pigment dispersions use is made for example of acrylate, methacrylate, styrene and vinyl polymers.

In a particularly preferred embodiment use is made of polyvinyl butyrate for ethanolic dispersions and of methyl methacrylate for dispersions with methyl ethyl ketone as solvent, or to copolymers of methyl methacrylate and butyl acrylate for pigment dispersions with chloroform as solvent.

Preferred polymers for aqueous pigment dispersion are composed for example of carboxyl-containing polymers, for example styrene, vinyltoluene and vinylbenzoic acid, or vinylbenzoic acid and apolar monomers, and of styrene and maleic anhydride or of copolymers of long-chain alkenes ($C_{12}$-$C_{18}$) with maleic anhydride, for example styrene-maleic anhydride, styrene-vinyltoluene-vinylbenzoic acid or octadecene-maleic anhydride.

A preferred embodiment of the process of the invention relates to the preparation of aqueous basic pigment dispersions from a latent pigment with a solution of a copolymer comprising vinylbenzoic acid and a non-polar monomer or with a solution comprising a carboxyl-containing polymer.

There now follows a series of examples that serve to illustrate the invention.

EXAMPLE 1

2475 g of p-chlorobenzonitrile, 2181.6 g diisopropyl succinate and 2869.2 g sodium tert-butylate are placed at 20-25° C. in a 10000 ml "All In One Reactor"® of (Drais Mannheim Germany). Under stirring and nitrogen flow the mixture is heated to 100° C. within 60 minutes. From 80° C. onwards the reaction mixture becomes considerably thicker and is finally converted into a paste. From 80-85° C. onwards a rapid formation of alcohol vapours is observed. The temperature is maintained at 99° to 100° C. for three hours, thereby allowing the mixture of isopropyl alcohol and tert-butyl alcohol to distil off. The reaction mass becomes crumbly and finally largely disintegrates into an almost semi-powdery material. The reaction mixture is heated to 120° C. in 30 minutes and kept at 120° C. for 30 minutes. The mixture is cooled to 50° C. The material is emptied into a polyethylene sack, tightly fitted to the outlet of the reactor; affording 3248 g (90% of theory, based on p-chlorobenzonitrile) of pigment of the formula XIX. Approximately 200 g (5.54% of theory, based on p-chlorobenzonitrile) of the product are still contained in the reactor to be used in the next batch. The total yield thus corresponds to approximately 3448 g (approximately 95.54% of theory, based on p-chlorobenzonitrile).

This product produces an intense red colour when dispersed with stirring into a state-of-the-art waterborne paint system.

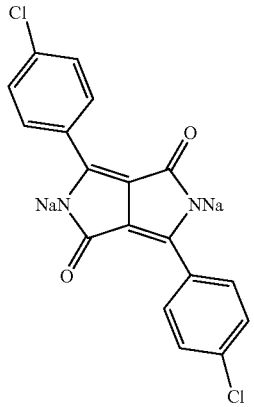

XIX

EXAMPLE 2

For the hydrolysis, 1000 g product of the example 1 are slowly added to a mixture of 7000 ml of methanol and 35 g of acetic acid at room temperature. The mixture is then heated to reflux and kept at reflux temperature for two hours. The resultant pigment suspension is filtered at about 50° C., washed with methanol and water until the washings run colourless, and dried at 80° C. in vacuum, affording 845 g (95% of theory, based on compound of formula XIX) of pure pigment of the formula XX

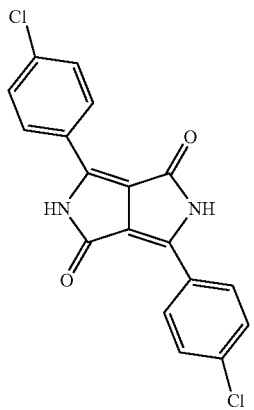

XX which colours PVC-red.

EXAMPLE 3

1545 g of benzonitrile, 2242.5 g di-tert-butyl succinate and 3024 g potassium tert-butylate are placed at 20-25° C. in a 10000 ml "All In One Reactor" of (Drais Mannheim Germany). Under stirring and nitrogen flow the mixture is heated to 100° C. within 60 minutes. From 700 onwards the reaction mixture becomes considerably thicker and is finally converted into a paste. From 70-75° onwards a rapid formation of alcohol vapours is observed. The temperature is maintained at 99 degree to 100° C. for three hours thereby allowing, the tert-butyl alcohol to distil off. The reaction mass becomes crumbly and finally largely disintegrates into an almost semi-powdery material. The reaction mixture is heated to 120° C. in 30 minutes and kept at 120° C. for 30 minutes. The mixture is cooled to 50° C. The material is emptied into a polyethylene sack, tightly fitted to the outlet of the reactor and then worked up as in example 2 yielding 1840 g (85% of theory, based on benzonitrile) of pure pigment of the formula XXI

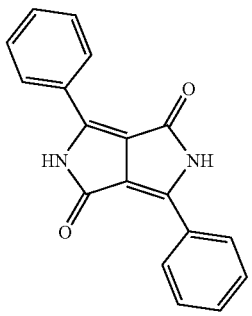

XXI

EXAMPLE 4

2750 g of p-chlorobenzonitrile and 2950 g sodium isopropylate are placed at 20-25° C. in a 10000 ml "All In One Reactor" of (Drais Mannheim Germany). Under stirring and nitrogen flow the mixture is heated to 90° C. within 60 minutes. As soon as this temperature has been reached, 2424 g diisopropyl succinate are added over 145 minutes by means of a metering pump. The temperature is kept constantly at 98-99° C. and isopropyl alcohol is distilled off. The temperature is maintained at 99 to, 100° C. for two hours. The reaction mixture is heated to 120° C. in 30 minutes and kept at 120° C. for 30 minutes. The mixture is cooled to 50° C. The material is emptied into a polyethylene sack, tightly fitted to the outlet of the reactor; the yield is 3490 g (approximately 87% of theory, based on p-chlorobenzonitrile) of the compound of formula XIX.

For the hydrolysis, 1000 g of the above reaction mixture is slowly added to 10000 ml of water at 80° C. temperature. The resultant pigment suspension is heated to 95° C. and kept at 95° C. for two hours. Thereafter, it is filtered at about 80° C., washed with water until the washings run colourless, and dried at 80° C. in vacuum; affording 872 g (98% of theory, based on the compound of formula XIX) of a very finely divided pigment of the formula XX.

The crude pigment is then finished by treating with seven volume parts of dimethyl formamide at 130° C. for three hours. The suspension is filtered at 100° C., washed with the same volume of dimethyl formamide heated to 110° C. followed by water at 70° C. The press cake is dried at 100° C. yielding a bright red product.

EXAMPLES 5-15

2-kilo mole of a nitrile of the formula R—CN, wherein R has the meaning indicated in Table 1, and 3960 g of sodium tert-amylate are placed at 20-25° C. in a 10000 ml paddle drier (TurbuDry®, Drais Mannheim Germany) The mixture is heated under nitrogen to the temperature indicated in Table 1. As soon as this temperature has been reached, 2626 ml of di-isopropyl succinate are added by means of a metering pump over the period of time also indicated in Table 1 and with continuous stirring. The indicated temperature is maintained and the alcohol mixture formed is allowed to distil off. When the addition is complete, the reaction mixture is kept at the same temperature for 2 hours and hydrolysed and worked up as in Example 2 to give the pigments of the formula XXII

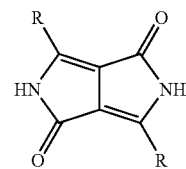

XXII wherein R has the meaning given in Table 1, in the indicated yield.

TABLE 1

| Example | R | Reaction Temperature °C. | Addition Time in Minutes | Yield based on Nitrile | Shade in PVC (0.1%) |
|---|---|---|---|---|---|
| 5 | Br—C₆H₄— | 98-100 | 120 | 81.5 | Red |
| 6 | H₃C—C₆H₄— | 90-92 | 130 | 75.9 | Red |
| 7 | tBu—C₆H₄— | 95-97 | 180 | 73.2 | Orange |
| 8 | Ph—C₆H₄— | 105-110 | 240 | 62.1 | Reddish-Violet |
| 9 | 3-NC—C₆H₄— | 90-95 | 100 | 51.1 | Yellowish Red |
| 10 | 3-F₃C—C₆H₄— | 105-110 | 120 | 58.3 | Red |
| 11 | 4-F₃C—C₆H₄— | 107-112 | 110 | 61.7 | Red |
| 12 | 1-naphthyl | 95-97 | 90 | 25.6 | Orange |
| 13 | 3-pyridyl | 90-92 | 60 | 45.5 | Red |
| 14 | 4-pyridyl | 90-95 | 90 | 32 | Red |

TABLE 1-continued

| Example | R | Reaction Temperature °C. | Addition Time in Minutes | Yield based on Nitrile | Shade in PVC (0.1%) |
|---|---|---|---|---|---|
| 15 | 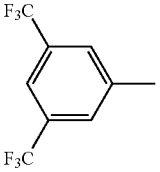 | 99-100 | 63 | 37 | Red |

EXAMPLES 16-20

1.0 mole of a nitrile of the formula R'—CN and 1.0 kilo mole of the formula R"—CN, wherein R' and R" are different and are as defined in Table II (Examples 16-20) and 3.4 kilo mole of sodium tert-amylate are placed at 20-25° C. in a 10000 ml "All In One Reactor"® (of Drais Mannheim Germany). By means of a metering pump, 1.2 kilo moles of diisopropyl succinate are added at the reaction temperature indicated in Table II over the period of time also indicated therein, while continuously distilling off the alcohol mixture. When the addition is complete, the mixture is kept for 2 hours at the reaction temperature and then hydrolysed and worked up as in Example 2 to give the pigment mixture of the formulas XXIII, XXIV and XXV of Table 2.

TABLE 2

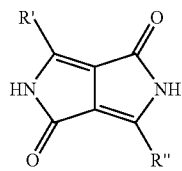

XXIII

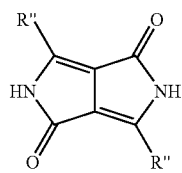

XXIV

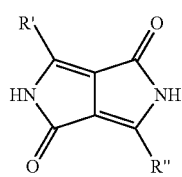

XXV

| Example | R' | R" | Reaction Temperature °C. | Yield in % of Nitrile | Shade in PVC (0.2%) |
|---|---|---|---|---|---|
| 16 | phenyl | 4-chlorophenyl | 95-100 | 69.7 | Red |
| 17 | 4-methylphenyl | 4-chlorophenyl | 95-100 | 57.7 | Scarlet |
| 18 | 4-chlorophenyl | 4-biphenyl | 105-110 | 39.6 | Bluish Red |

TABLE 2-continued

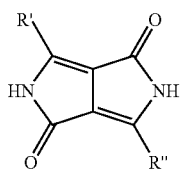

XXIII

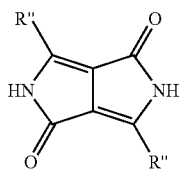

XXIV

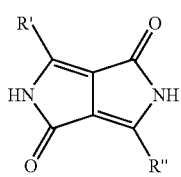

XXV

| Example | R' | R" | Reaction Temperature °C. | Yield in % of Nitrile | Shade in PVC (0.2%) |
|---|---|---|---|---|---|
| 19 | 3-chlorophenyl | 4-chlorophenyl | 95-100 | 82.7 | Red |
| 20 | 4-methylphenyl | 4-tert-butylphenyl | 110-115 | 67 | Orange |

EXAMPLE 21

1786 g of the crude diketopyrrolopyrrole pigment C.I. Pigment Red 254, 3000 g of tert-butyl alcohol and 960 g of sodium tert-butylate are placed in a 10000 ml "All In One Reactor"® of (Drais Mannheim Germany) at 30° C. Under stirring and nitrogen flow the mixture is heated to 80° C. and maintained at 80 for 1 hour. From 50° C. onwards the reaction mixture becomes considerably thicker and is finally converted into a paste. Thereafter, the mixture is slowly heated from outside to approx. 90° C. After reaching an inside temperature of 85 C a vacuum of 800 mbar is applied at the outlet of the condenser which is then gradually reduced to 50 mbar, thereby allowing the tert-butyl alcohol to distil off. The reaction mass becomes crumbly and finally largely disintegrates into an almost semi-powdery material. The mixture is stirred for another 30 minutes at 90° C. under vacuum of 50 mbar. The reaction mixture is cooled to 80° C. The material is emptied into a steel drum affording 1950 g of the product of the formula XIX. Approximately 60 g of the product are still contained in the reactor to be used in the next batch. The distillate is also used for the next batch.

EXAMPLES 22-26

Using the corresponding commercially available crude pigments in place of Pigment Red 254 in example 21 and/or the corresponding molar quantity of potassium tert-butylate in place of sodium tert-butylate, the following compounds of general formula XXVI of Table 3 are obtained

TABLE 3

XXVI

[Structure: pyrrolo-pyrrole dione with Ra substituents and MN groups]

| Example | Starting Material | Ra | M | Color of Solid |
|---------|------------------|-----|-----|----------------|
| 22 | Pigment Red 255 | phenyl | Na | Red |
| 23 | Pigment Red 264 | biphenyl | Na | Bluish Red |
| 24 | Pigment Orange 73 | 2,4,6-trimethylphenyl ((H₃C)₃-phenyl) | Na | Orange |
| 25 | Pigment Red 272 | 4-methylphenyl (H₃C-phenyl) | K | Red |
| 26 | Pigment Red 71 | 3-cyanophenyl (NC-phenyl) | Na | Orange |

EXAMPLE 27

1527.4 g diisopropyl succinate, 1732.5 g of p-chlorobenzonitrile and 2013 g sodium tert-butylate are placed in a 10000 ml "All In One Reactor"® of (Drais Mannheim Germany) at 20-25° C. Under stirring and nitrogen flow the mixture is heated to 87° C. (inside temperature). From 50° C. onwards the reaction mixture becomes considerably thicker and is finally converted into a paste. As soon as the inside temperature of 87° C. is reached, a vacuum of 800 mbar is applied at the outlet of the condenser which is then gradually reduced to 50 mbar, thereby allowing the mixture of isopropyl alcohol and tart-butyl alcohol to distil off. The inside temperature first drops to 75° C. and thereafter rises again to 85° C. as soon as the mixture of alcohols is completely distilled off. The reaction mass becomes crumbly and finally largely disintegrates into an almost semi-powdery material. After the distillation of the residual mixture of alcohols, the reaction mixture is stirred for another 30 minutes at 87° C. under vacuum of 50 mbar. The mixture is cooled to 60° C. and the material is emptied into a steel container. The yield is 2950 g of the crude compound of formula XIX of example 21 of 81.4% purity (approximately 95% of theory, based on p-chlorobenzonitrile).

EXAMPLES 28-33

Using the corresponding nitriles of formula VI in place of p-chlorobenzonitrile in example 27 the following compounds of Table 4 are obtained

TABLE 4

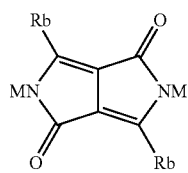

XXVII

| Example | $R_b$ | M | Color of Solid |
|---------|-------|---|----------------|
| 28 | 3,4-dimethylphenyl (H₃C, H₃C) | Na | Red |
| 29 | 3,5-dichlorophenyl (Cl, Cl) | Na | Red |
| 30 | 3-chloro-4-methylphenyl (H₃C, Cl) | Na | Red |

TABLE 4 (continued)

| | | | |
|---|---|---|---|
| 31 | 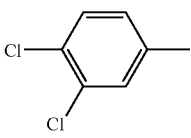 | Na | Red |
| 32 | 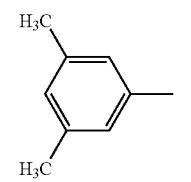 | Na | Red |
| 33 | 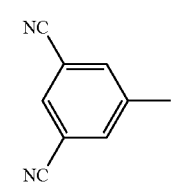 | K | Red |

EXAMPLE 34

For the hydrolysis, 1000 g product of the crude compound of formula XIX of example 27 is slowly added to a mixture of 7000 ml of methanol and 330 g of acetic acid at room temperature. The mixtures is then heated to reflux and kept at reflux temperature for two hours. The resultant pigment suspension is filtered at about 50° C., washed with methanol and water until the washings run colourless, and dried at 80° C. in vacuum, affording 720 g of the pure pigment of formula XX.

EXAMPLES 35-40

Using the corresponding starting materials of Table 4 (examples 28-33) in example 27 the compounds of Formula XXVIII in Table 5 are obtained

TABLE 5

XXVIII

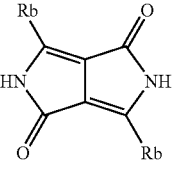

| Example | Starting Material | $R_b$ | M | Color of Solid |
|---|---|---|---|---|
| 35 | Example 28 | 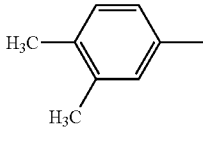 | Na | Orange-Red |
| 36 | Example 29 | 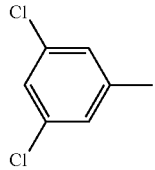 | Na | Red |
| 37 | Example 30 | 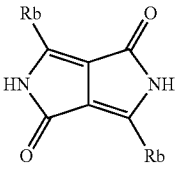 | Na | Red |
| 38 | Example 31 | 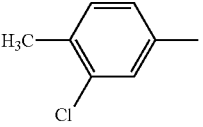 | Na | Orange-Red |
| 39 | Example 32 | 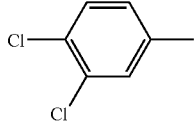 | Na | Orange-Red |
| 40 | Example 33 | 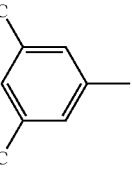 | K | Red |

EXAMPLE 41

Compound of formula XX, obtained by using compound of formula XIX of Example 21 as starting material in example 34

EXAMPLES 42-46

Compounds of formula XXIX (Table 6), obtained by using the corresponding compounds of formula XXVI of Table 3 as starting materials in example 34

TABLE 6

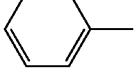

| Example | Starting Material | Ra | Color of Solid |
|---|---|---|---|
| 42 | Example 22 | 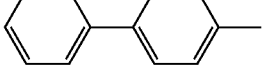 | Red |
| 43 | Example 23 | 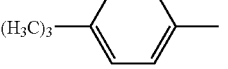 | Bluish Red |
| 44 | Example 24 | (H$_3$C)$_3$—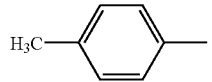 | Orange |
| 45 | Example 25 | H$_3$C—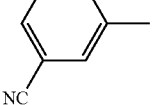 | Red |
| 46 | Example 26 | NC—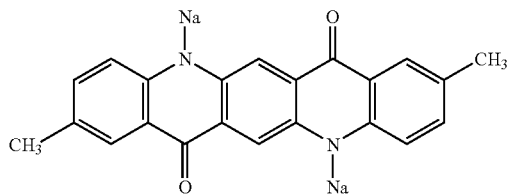 | Orange |

EXAMPLE 47

A 500 ml glass reactor is charged with 150 ml of anhydrous ter-amyl alcohol under nitrogen. 4.6 g (0.2 moles) of sodium are added thereto and the mixture is heated to and maintained at 100-105° C. for 12 hours. To the resulting solution are then added at 80° C., 20.6 g (0.15 moles) of 4-chlorobenzonitrile. Subsequently 20.1 g (0.01 moles) of diisopropyl succinate are metered in at 96° C. over 3 hours. The isopropanol formed during the reaction along with some tert-amyl alcohol is allowed to distil off simultaneously during the addition. The reaction mixture is stirred for another 4 hours after the addition of diisopropyl succinate is complete. Thereafter the reaction mixture is transferred to a 500 ml round bottomed flask and the residual tert-amyl alcohol is distilled off on a rotavap (Buechi) under vacuum to yield the compound of Formula XIX as a dark red powder.

EXAMPLE 48

Hydrolysis of the compound XIX of example 47 to a compound of Formula XX as described in example 34

EXAMPLE 49

1700 g of the crude dimethyl quinacridone pigment C.I. Pigment Red 122, 3500 g of tert-butyl alcohol and 960 g of sodium tert-butylate are placed in a 10000 ml "All In One Reactor"® of (Drais Mannheim Germany) at 30 C. Under stirring and nitrogen flow the mixture is heated to 80° C. and maintained at 80° C. for 3 hours. From 50° C. onwards the reaction mixture becomes considerably thicker and is finally converted into a paste. Thereafter, the mixture is slowly heated to approx. 90° C. After reaching an inside temperature of 85° C. a vacuum of 800 mbar is applied at the outlet of the condenser which is then gradually further reduced to 50 mbar, thereby allowing the tert-butyl alcohol to distil off. The inside temperature first drops to 75° C. and thereafter rises again to 85° C. as soon as the alcohol is completely distilled off. The reaction mass becomes crumbly and finally largely disintegrates into an almost semi-powdery material. The mixture is stirred for another 30 minutes at 85° C. under vacuum of 50 mbar. The reaction mixture is cooled to 60° C. The material is emptied into a steel drum affording 1890 g of the product of the formula XXX.

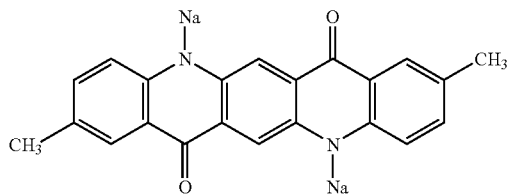

Approximately 30 g of the product are still contained in the reactor to be used in the next batch. The distillate is also used for the next batch.

EXAMPLES 50-53

Starting from the corresponding Pigments, compounds of Table 7 are obtained following the procedure described in Example 49

TABLE 7

| Example | Starting Material | Product | Formula |
|---|---|---|---|
| 50 | Pigment Yellow 138 | | XXXI |
| 51 | Pigment Yellow 110 | | XXXII |
| 52 | Pigment Yellow 109 | | XXXIII |
| 53 | Pigment Yellow 139 | | XXXIV |

EXAMPLE 54

To a mixture of 400 ml of water, 1.6 g of phthalic acid, 0.7 g of a 2% (percent by weight) solution of a surface-active substance (Fluorad FC-171 from 3M Inc.) dissolved in diethylene glycol are added 4 g of the compound of formula XIX of Example 21 under stirring followed by the addition of 10 g of octadecene-maleic anhydride copolymer (MW 50 000, from Scientific Polymer Products Inc.) dissolved in 100 ml of dioxane. After mixing, dioxane is distilled off on a rotary evaporator under reduced pressure and the red dispersion is concentrated to approximately 410 g. The resulting dispersion is homogeneous and transparent. It has a viscosity of 2.16 mPas at 25.degree. C. After several days, no tendency to precipitate is observed. A sample is diluted 50-fold with water and the transmission spectrum is measured in a 1 mm cell. At the maximum (520 nm) the absorption is 1.42, while at 660 nm it is only 0.1, which points to fine particles with good transparency. In addition, electron micrographs show that all particle dimensions are below 0.5 micrometers.

EXAMPLE 55

3 g of the pigment dispersion of Example 54 are mixed with 0.75 g of a 2% (percent by weight) solution of a surface-active substance (Fluorad FC-171 from 3M Inc.) dissolved in diethylene glycol. The resulting ink is tested in a "Quietjet" (Hewlett-Packard) thermal inkjet printer, which is fitted with a plastic device provided to accommodate the ink. A clear, sharp print quality is obtained, as is a surface coverage at a peak optical density of 0.5 (this value is measured with a spectrometer in reflection mode, which is subtracted from the reflection of the paper).

The ink shows no tendency to bleed or penetrate through customary commercial copier paper.

EXAMPLE 56

10 g of the pigment dispersion of Example 54 are mixed with 0.8 g of a 2% (percent by weight) solution of a surface-active substance (Fluorad FC-171 from 3M Inc.) and diethylene glycol and with 1.2 g of diethylene glycol, 0.5 g of 2-propanpol, 0.2 g of morpholine and 0.2 g of butyl sulfoxide. The resulting ink is tested in a "QuietJet" (Hewlett-Packard) thermal inkjet printer, which is fitted with a plastic device provided to accommodate the ink. A clear, sharp print quality is obtained, as is a surface coverage with a maximum optical density of 1.09 (this value is measured with a spectrometer in reflection mode, which is subtracted from the reflection of the paper).

The ink shows no tendency to bleed or penetrate through customary commercial copier paper.

EXAMPLE 57

To a mixture of 25 parts of a styrene/acrylic acid copolymer acrylate resin (for example as described in WO 03/08510), 5 parts of a dispersant $(C_{13-15}\text{-alkyl})\text{-O}\text{---}(CH_2CH_2O)_{9.5}\text{---}CH_2COONa$, 15 parts of propylene glycol and 35 parts of water are added 20 parts of a compound of formula XIX of example 21 under stirring. To the resulting mixture is then added 8 parts of phthalic acid. The resulting pigment dispersion does not need to be milled using for example a sand mill.

The pigment dispersion shows excellent flow properties and storage stability. It is particularly suitable for ink-jet applications.

EXAMPLE 58

20 parts of the compound XIX of example 21 was added to a mixture of 30 parts of propylene glycol monomethyl ether acetate and 50 parts of an acrylic resin (obtained by polymerizing methacrylic acid, butyl acrylate, styrene, hydroxyethyl acrylate at a molar ratio of 25/50/15/10; molecular weight: 12,000; solid content: 30%) and 8.3 parts of terephthalic acid. Thereby a red base color for color filters was obtained (for example of U.S. Pat. No. 6,302,953 without a dispersant).

EXAMPLE 59

40 parts of the compound of formula XIX of example 21 are added to a mixture of 7.5 parts of a polyphenyloxalate, 7.5 parts of α-methyl-omega-hydroxy-polyethylenglykolether (MW 470-530 g/mol) and 45 parts of water under stirring followed by the addition of 15.75 parts of trimesic acid. The resulting pigment dispersion does not need to be milled using for example a sand mill.

The pigment dispersion shows excellent flow properties and storage stability. It is particularly suitable for tinting of architectural paints.

The invention claimed is:

1. A process for the preparation of a compound of formula III

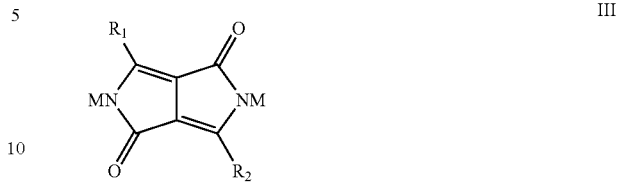

wherein both M represent an alkali metal and each of $R_1$ and $R_2$ independently of the other is a carbocylic aromatic radical or a heterocyclic aromatic radical, which process comprises the steps of: providing to a reactor as reactants an unsymmetrical or symmetrical dialkyl or diaryl succinate, or monoalkyl monoaryl succinate or dicycloalkyl succinate of formula V

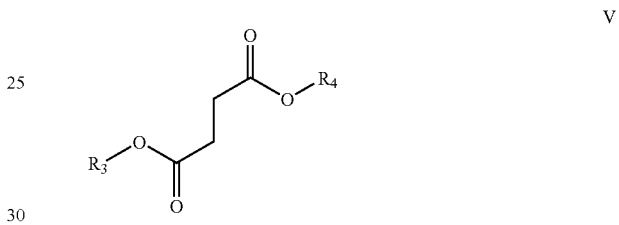

wherein each $R_3$ and $R_4$ independently of the other is an alkyl or a cycloalkyl or an aryl radical, with two moles of nitrile of formula VI $R_1$—CN    (VI)

or of formula VII $R_2$—CN    (VII)

for at least each mole of succinate or with 0.0 to 2.0 mole of a nitrile of the formula (VI) and 2.0 to 0.0 mole of the nitrile of the formula (VII), and further, providing 2 to 5 moles of a strong base at a temperature of 20° C.-25° C., then subsequently reacting the said reactants in the presence of the strong base and essentially in the absence of any organic solvent to condense the reactants at a temperature of 70° C. to 200° C.

2. A process according to claim 1, wherein essentially no organic solvent is present.

3. A process according to claim 1, wherein said strong base is an alkali metal, an alkali metal amide, an alkali metal hydride, an alkali metal alcoholate or an alkaline earth metal alcoholate.

4. A process according to claim 1, wherein the nitrile is a single nitrile of the formula VI or VII.

5. A process according to claim 1, wherein the disuccinate V is a symmetrical dialkyl succinate containing 1 to 18 carbon atoms in each alkyl moiety.

6. A process according to claim 1, wherein the disuccinate V is a symmetrical dialkyl succinate, wherein alkyl is sec- or tert-alkyl.

7. A process according to claim 1 wherein each of $R_1$ and $R_2$ independently of the other is phenyl or phenyl substituted by one or two chlorine atoms, by one or two methyl groups, by methoxy, by trifluoromethyl, by cyano, by methoxycarbonyl, by tert-butyl, by dimethylamino or by cyanophenyl; naphthyl; biphenylyl; pyridyl or said pyridyl substituted by amyloxy; furyl or thienyl.

8. A process according to claim 7 wherein each of $R_1$ and $R_2$ independently of the other is phenyl, 3-chlorophenyl, 4-chlorophenyl, 3,5-dichlorophenyl, 4-methylphenyl, 4-methoxyphenyl, 3-trifluoromethylphenyl, 4-trifluoromethylphenyl, 3-cyanophenyl, 4-cyanophenyl, 4-methoxycarbonylphenyl, 4-tert-butylphenyl, 4-dimethylaminophenyl, 4-(p-cyanophenyl) phenyl, 1-naphthyl, 2-naphthyl, 4-biphenylyl, 2-pyridyl, 3-pyridyl, 4-pyridyl, 6-amyloxy-3-pyridyl, 2-furyl or 2-thienyl.

9. A process according to claim 1, wherein the strong base is an alkali metal alcoholate.

10. A process according to claim 9, wherein the alkali metal alcoholate is derived from a secondary or tertiary alcohol.

* * * * *